US010557826B2

United States Patent
Kuhnen et al.

(10) Patent No.: US 10,557,826 B2
(45) Date of Patent: Feb. 11, 2020

(54) VIBRONIC SENSOR (71) Applicant: Endress + Hauser GmbH + Co. KG, Maulburg (DE)

(72) Inventors: Raphael Kuhnen, Schliengen (DE); Ira Henkel, Wehr (DE); Peter Wimberger, Schopfheim (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 213 days.

(21) Appl. No.: 15/521,625

(22) PCT Filed: Sep. 2, 2015

(86) PCT No.: PCT/EP2015/070029
§ 371 (c)(1),
(2) Date: Apr. 25, 2017

(87) PCT Pub. No.: WO2016/066305
PCT Pub. Date: May 6, 2016

(65) Prior Publication Data
US 2017/0241954 A1 Aug. 24, 2017

(30) Foreign Application Priority Data
Oct. 29, 2014 (DE) .................. 10 2014 115 693

(51) Int. Cl.
*G01F 23/296* (2006.01)
*G01N 11/16* (2006.01)
(Continued)

(52) U.S. Cl.
CPC ....... *G01N 29/022* (2013.01); *G01F 23/2967* (2013.01); *G01F 23/2968* (2013.01);
(Continued)

(58) Field of Classification Search
CPC ............ G01F 23/2968; G01F 23/2967; G01N 29/022; G01N 11/16; G01N 29/07;
(Continued)

(56) References Cited

U.S. PATENT DOCUMENTS 3,229,523 A 1/1966 Boyd
5,408,168 A * 4/1995 Pfandler ............... B06B 1/0618
310/323.21
(Continued)

FOREIGN PATENT DOCUMENTS

CA 2277595 A1 2/2001
CN 1682097 A 10/2005
(Continued)

OTHER PUBLICATIONS

R. Oria, J. Otero, L. Gonzalez, L. Botaya, M. Carmona, M. Puig-Vidal "Finite Element Analysis of Electrically Excited Quartz Tuning Fork Devices", Dept. of Electronics, University of Barcelona, Barcelona, Spain, May 30, 2017.
(Continued)

*Primary Examiner* — Jacques M Saint Surin
(74) *Attorney, Agent, or Firm* — Bacon & Thomas, PLLC (57) ABSTRACT

An apparatus for determining and/or monitoring at least one process variable of a medium in a container, comprising at least an oscillatable unit having at least one membrane, and at least one oscillatory element, a driving/receiving unit embodied to excite the mechanically oscillatable unit by means of an electrical, exciter signal of adjustable excitation frequency to execute oscillations in an oscillation mode corresponding to the excitation frequency and to receive mechanical oscillations from the oscillatable unit and to convert such into an electrical received signal, and an electronics unit embodied, to produce the exciter signal, and to ascertain from the received signal the at least one process
(Continued)

variable. The membrane is connected with the driving/receiving unit. The oscillatory element has the shape of an oscillatory rod, on which a paddle is terminally formed, and the oscillatory element is secured on the membrane in an end region remote from the paddle. Mass distribution, stiffness and/or geometry of the oscillatable unit is/are selected in such a manner that at least one of the oscillation modes of the oscillatable unit higher in reference to the oscillation mode corresponding to the excitation frequency lies in the range between two neighboring whole-numbered multiples of the excitation frequency.

11 Claims, 5 Drawing Sheets

(51) Int. Cl.
```
G01N 29/22      (2006.01)
G01N 29/46      (2006.01)
G01N 29/07      (2006.01)
G01N 9/00       (2006.01)
G01N 29/02      (2006.01)
```
(52) U.S. Cl.
CPC ............ *G01N 9/002* (2013.01); *G01N 11/16* (2013.01); *G01N 29/07* (2013.01); *G01N 29/222* (2013.01); *G01N 29/46* (2013.01); G01N 2009/006 (2013.01); G01N 2291/014 (2013.01); G01N 2291/015 (2013.01); G01N 2291/02818 (2013.01); G01N 2291/0427 (2013.01)

(58) Field of Classification Search
CPC ...... G01N 9/002; G01N 29/46; G01N 29/222; G01N 2009/006; G01N 2291/014; G01N 2291/015; G01N 2291/02818; G01N 2291/0427
USPC .......................................................... 73/584
See application file for complete search history.

(56) References Cited

U.S. PATENT DOCUMENTS

| | | | |
|---|---|---|---|
| 5,631,633 A * | 5/1997 | Dreyer | ............... G01F 23/2967 310/323.21 |
| 6,938,475 B2 | 9/2005 | Lopatin | |
| 6,997,052 B2 * | 2/2006 | Woehrle | ............... G01F 23/2967 73/290 R |
| 7,102,528 B2 * | 9/2006 | Pfeiffer | ............... G01F 23/2967 318/642 |
| 7,403,127 B2 * | 7/2008 | Pfeiffer | ............... G01F 23/2968 318/648 |
| 7,681,445 B2 * | 3/2010 | Pfeiffer | ............... G01F 23/2965 73/290 V |
| 8,220,313 B2 | 7/2012 | Lopatin | |
| 8,955,377 B2 | 2/2015 | Hortenbach | |
| 2010/0030486 A1 | 2/2010 | Lopatin | |

FOREIGN PATENT DOCUMENTS

| | | |
|---|---|---|
| DE | 4203967 A1 | 8/1993 |
| DE | 10153937 A1 | 2/2003 |
| DE | 1373840 B1 | 1/2004 |
| DE | 10242970 A1 | 4/2004 |
| DE | 102005062001 A1 | 6/2007 |
| DE | 102006033819 A1 | 1/2008 |
| DE | 102007057124 A1 | 7/2008 |
| DE | 102009026685 A1 | 12/2010 |
| DE | 102014115693 A1 | 5/2016 |

OTHER PUBLICATIONS

German Search Report, German Patent Office, Munich, DE, dated Jul. 21, 2015.
International Search Report, EPO, The Netherlands, dated Nov. 4, 2015.
English Translation of the International Preliminary Report on Patentability, WIPO, Geneva, CH, dated May 11, 2017.
Chinese Office Action in corresponding Chinese Application No. 201580058179.9, dated Dec. 27, 2018.

* cited by examiner

VIBRONIC SENSOR

TECHNICAL FIELD

The invention relates to an apparatus and to a method for monitoring at least one process variable of a medium with at least one oscillatable unit having a membrane and an oscillatory element.

BACKGROUND DISCUSSION

Such apparatuses, also referred to as vibronic sensors, are applied as fill level measuring devices and have frequently an oscillatory fork as an oscillatable unit. However, also variants with a single rod or a membrane are known. The oscillatable unit is excited during operation by means of an electromechanical transducer unit to execute mechanical oscillations. The electromechanical transducer unit can be, for example, a piezoelectric drive or an electromagnetic drive.

Of course, besides the mentioned examples, also other options are available, which likewise fall within the scope of the present invention.

Corresponding field devices are sold by the applicant in many different forms. In the case of fill-level measuring devices, for example, devices of such type are sold under the marks, LIQUIPHANT and/or SOLIPHANT. The underpinning measuring principles are known from a large number of publications. The exciting of the oscillatable unit can be performed both by means of analog as well as also digital methods and occurs most often via an analog, electrical, oscillatory circuit. The electromechanical transducer unit excites the oscillatable unit by means of an electrical, exciter signal to execute mechanical oscillations and receives the oscillations and transduces them into an electrical, received signal. The electromechanical transducer unit can be either separate driving- and receiving units or a combined driving/receiving unit.

In such case, the electromechanical transducer unit is part of a control loop integrated in an electronics unit. The control loop sets the exciter signal in the normal case in such a manner that a predeterminable phase shift is present between the exciter signal and received signal. For example, for resonant oscillation, the oscillatory circuit condition must be fulfilled, according to which all phases arising in the oscillatory circuit yield a multiple of 360°.

Both exciter signal as well as also received signal are characterized by frequency, amplitude and/or phase. Therefore, changes in these variables are usually taken into consideration for determining the respective process variable, such as, for example, a predetermined fill level of a medium in a container, or also the density and/or viscosity of a medium. In the case of a vibronic limit level switch for liquids, it is distinguished, for example, whether the oscillatable unit is covered by the liquid or is freely oscillating. These two states, the free state and the covered state, are distinguished, in such case, based on different resonance frequencies, thus a frequency shift. Density and/or viscosity, in turn, can be ascertained with such a measuring device only in the case of an at least partial covering with the medium.

Used as exciter signal are usually sine- or rectangular signals. The advantage of a sinusoidal signal is that no, or few, overtones, which are whole-numbered multiples of the exciting signal, are transmitted to the oscillatable unit. In this way, the provided oscillatory energy is advantageously used essentially for only one oscillatory mode. With reference to the signal production within the electronics unit, this is, however, comparatively complicated and associated with a comparatively higher power consumption of the measuring device. Therefore, expediently, in general, a rectangular signal is used for the excitation. This enables, especially, that vibronic measuring devices can be operated via 4-20 mA- or NAMUR-interfaces.

A disadvantage of using rectangular signals, however, is that, besides the excitation frequency, also overtones are transmitted to the oscillatable unit. As a result, considerable noise can emanate from the oscillatable unit.

For the majority of all applications, the desired oscillatory mode is the fundamental oscillation mode, which is excited by exciting with the fundamental resonance frequency. However, also known are applications, in the case of which the torsion mode is excited.

SUMMARY OF THE INVENTION

An object of the present invention is to provide an oscillatable unit, as well as a method for its manufacture, for a vibronic sensor, which is distinguished by a low noise emission, especially in the case of exciting with a rectangular signal.

This object of the invention is achieved by an apparatus for determining and/or monitoring at least one process variable of a medium in a container, comprising at least an oscillatable unit having at least one membrane and at least one oscillatory element, a driving/receiving unit, which is embodied to excite the mechanically oscillatable unit by means of an electrical, exciter signal of adjustable excitation frequency to execute oscillations in an oscillation mode corresponding to the excitation frequency and to receive mechanical oscillations from the oscillatable unit and to convert such into an electrical received signal, and an electronics unit, which is embodied, based on the received signal, to produce the exciter signal, and to ascertain from the received signal the at least one process variable, wherein the membrane is connected with the driving/receiving unit, wherein the oscillatory element has the shape of an oscillatory rod, on which a paddle is terminally formed, and the oscillatory element is secured to the membrane in an end region of the oscillatory element remote from the paddle, and wherein mass distribution, stiffness and/or geometry of the oscillatable unit is/are selected in such a manner that at least one of the oscillation modes of the oscillatable unit higher in reference to the oscillation mode corresponding to the excitation frequency lies in the range between two neighboring whole-numbered multiples of the excitation frequency.

This measure significantly reduces noise emission based on the following considerations: Especially in the case of excitation with a rectangular signal, a number of overtones are transmitted to the oscillatable unit. If the frequencies of the overtones in the exciter signal correspond to a frequency for exciting a higher oscillatory mode of the oscillatable unit, then a number of oscillation modes superimpose instead of a single oscillation in the desired oscillatory mode. This leads then to the increased noise emission. It is, thus, advantageous, when the fundamental resonance frequency of the oscillatable unit, as well as the harmonics of the fundamental resonance frequency, thus the frequencies, with which the higher oscillation modes are excited, do not correspond to the overtones of the exciting signal.

Quite generally, the resonant frequency of a mechanical oscillatory system depends on its stiffness and mass distribution. The smaller the stiffness, the smaller is the oscillation frequency at constant mass. Thus, by an intelligent choice of the mass distribution, stiffness and/or geometry, the oscillation spectrum of the oscillatable unit can, with targeting, be changed and optimized for any particular application. Especially, it can advantageously be achieved that higher oscillation modes are not at frequencies corresponding to the overtones of the respective excitation frequency.

In an especially preferred embodiment, the oscillatable unit is an oscillatory fork. This embodiment of the oscillatable unit of a vibronic sensor is the most frequently applied geometry. This is due to the special oscillation characteristics, which the geometry of a tuning fork provides.

It is advantageous, when the paddle is composed of a predeterminable material with a density ($\rho$), and a predeterminable area ($A_P$) and a predeterminable thickness (d), and when the product of thickness (d) and density ($\rho$) is as small as possible, and the area ($A_P$) of the paddle is as large as possible. This combination of characteristics significantly increases the accuracy of measurement, such as described in German Patent, DE102005062001A1.

Likewise advantageous is when the area ($A_P$) of the paddle and/or of the oscillatory rod ($A_R$) is/are curved. This simplifies processing of the paddle, especially its polishing.

In a preferred embodiment, edges of the paddle are rounded. In such case, it is especially advantageous, when width of the paddle (b) is greatest in the middle region with reference to the longitudinal axis (L) parallel to the oscillatory rod, and the paddle in the end region remote from the membrane slopes at an angle between 20° and 55° relative to the longitudinal axis of the paddle. Paddles, which slope on the edges, especially in the end region, are advantageous with reference to the drop shedding characteristics of the oscillatable unit, especially in the case of clinging media, such as described in European Patent, EP1373840B1.

In another variant, the paddle can also have a pointed end. This geometry is, indeed, the most advantageous with reference to the drop shedding characteristics of the oscillatory fork. However, the sensitivity of the oscillatory fork sinks with declining area in the end region of the paddle, since the switching point for the detection of the exceeding of a limit level of a medium changes. The switching point is defined by a certain adjustable frequency shift, which corresponds to a certain immersion depth of the oscillatory fork in the medium. In the case of the conventional LIQUIPHANT instrument, the switching point lies, for example, about 13 mm above the end region of the two paddles.

Thus, it is advantageous, depending on application, to decide, which geometry brings the most advantages, and to balance whether the drop shedding behavior plays a meaningful role for the particular application.

In an additional preferred embodiment, the oscillatory rod of the oscillatory element has a round cross sectional area perpendicular to the longitudinal axis (L). The ideal coupling of the at least one oscillatory element to the membrane is point-shaped. This geometry is, however, technically not implementable. A round cross sectional area offers the best compromise in this regard.

In an additional embodiment, thickness of the paddle in the end region is less than in the middle region. Also this measure increases the measuring sensitivity of the oscillatory fork.

In a preferred embodiment, the at least one process variable is a predetermined fill level of the medium, or the density of the medium or the viscosity of the medium.

In an additional preferred embodiment, the oscillatable unit is manufactured of a metal, a ceramic or a synthetic material, e.g. a plastic. Of course, also other materials fall within the scope of the invention, and the oscillatory fork can be provided with a coating.

The object of the invention is further achieved by a method for manufacturing an oscillatable unit of the invention, wherein mass distribution, stiffness and/or geometry of the oscillatable unit is varied for adjusting the position of the at least one higher oscillation mode of the mechanically oscillatable unit, so that the higher oscillatory mode lies in the range between two neighboring whole-numbered multiples of the excitation frequency. The mass distribution, stiffness and/or geometry of the oscillatable unit is/are thus varied until the at least one higher oscillatory mode of the oscillatable unit is no longer excited by the overtones of the excitation frequency. A preferred method for constructing a suitable oscillatory fork is given by the finite elements method, which is a numerical method for solution of partial differential equations.

In the case of the method for manufacturing the oscillatable unit, it is advantageous, when for adjusting the position of the first higher oscillatory mode the mass distribution in the middle region of the paddle is varied. Likewise it is advantageous, when for adjusting the position of a higher oscillatory mode, especially the second higher oscillatory mode, the stiffness in the region of the membrane and the connection between membrane and oscillatory rod is varied.

The reason for this is based on the specific oscillatory movements, which the oscillatable unit executes in the particular oscillatory modes. This will be explained in the following using the example of a bending oscillator in the form a unilaterally clamped rod, such as also is the case for an oscillatory fork. If the bending oscillator is excited with the fundamental oscillation frequency, then it executes oscillations in the fundamental oscillation mode. In such case, the rod oscillates with a deflection amplitude, which is greatest on the end remote from the clamped end of the rod, while on the clamped end an oscillation nodes forms. If the bending oscillator is excited with frequencies corresponding to the higher oscillation modes, then, with each oscillatory mode, the number of oscillation nodes on the rod per oscillatory mode grows by at least one. Correspondingly, a further oscillation node occurs for the first excited oscillatory mode in the middle region of the bending oscillator, etc. The positions of the oscillation nodes in the separate oscillatory modes thus gives an indication of how, or where, mass distribution, stiffness and/or geometry of the oscillatable unit should best be varied. The taking into consideration of the specific oscillatory movement in a certain oscillatory mode significantly facilitates the calculative effort for finding the ideal mass distribution, stiffness and/or geometry.

BRIEF DESCRIPTION OF THE DRAWINGS

The invention as well as advantageous embodiments thereof will now be described in greater detail based on the appended drawing, the figures of which show as follows:

FIG. 2 is a schematic view (*a*) of an oscillatory fork as well as (*b*) the movements of an oscillatory fork in the fundamental oscillation mode as well as in the first two excited oscillation modes;

FIG. 3 (*a*) shows the oscillation spectrum of the oscillatory fork of a LIQUIPHANT field device in comparison with the oscillation spectrum of an oscillatory fork of the invention, and (*b*) shows the associated acoustic spectra;

FIG. 5 (a) shows a side view of the oscillatory fork of the invention of FIG. 4, (b) shows a second variant of an oscillatory fork of the invention with a paddle rounded in the end region, and (c) shows a third variant of an oscillatory fork of the invention with a paddle having a pointed end.

DETAILED DISCUSSION IN CONJUNCTION WITH THE DRAWINGS

Figure 1:
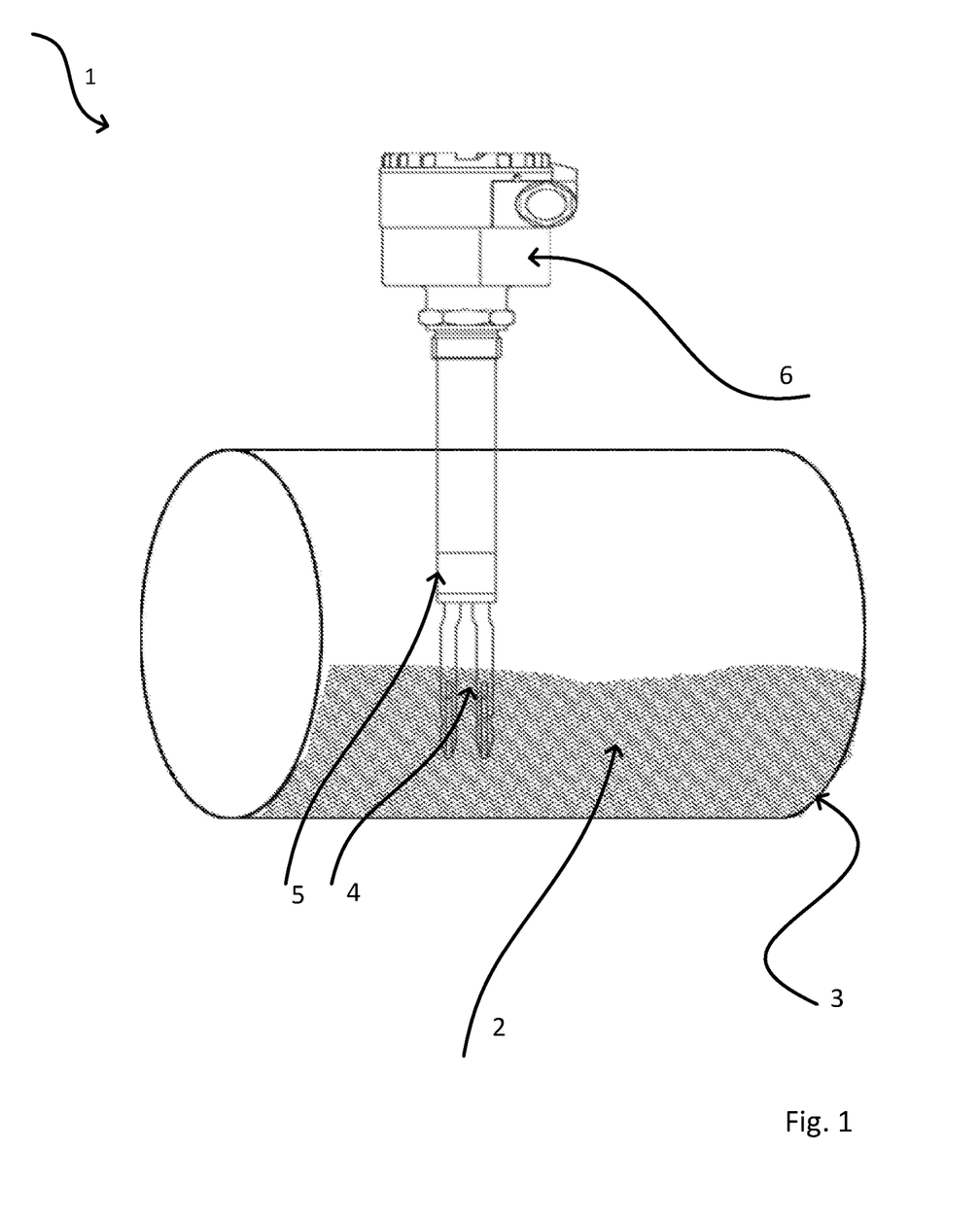
FIG. 1 is a schematic view of a vibronic sensor of the state of the art.

FIG. 1 shows a vibronic sensor 1. An oscillatable unit 4 in the form of an oscillatory fork extends partially into a medium 2 located in a container 3. Since this variant of the oscillatable unit is applied most frequently, the entire following description concerns, without limitation, an oscillatory fork.

The oscillatory fork is excited to execute mechanical oscillations by means of the electromechanical transducer unit 5, which is supplied with the exciter signal. The electromechanical transducer unit 5 can be, for example, a piezoelectric stack- or a bimorph drive. It is understood, however, that also other embodiments of a vibronic sensor fall within the scope of the invention. Furthermore, an electronics unit 6 is shown, by means of which the signal evaluation and/or supply of the exciter signal occurs.

Figure 2A:
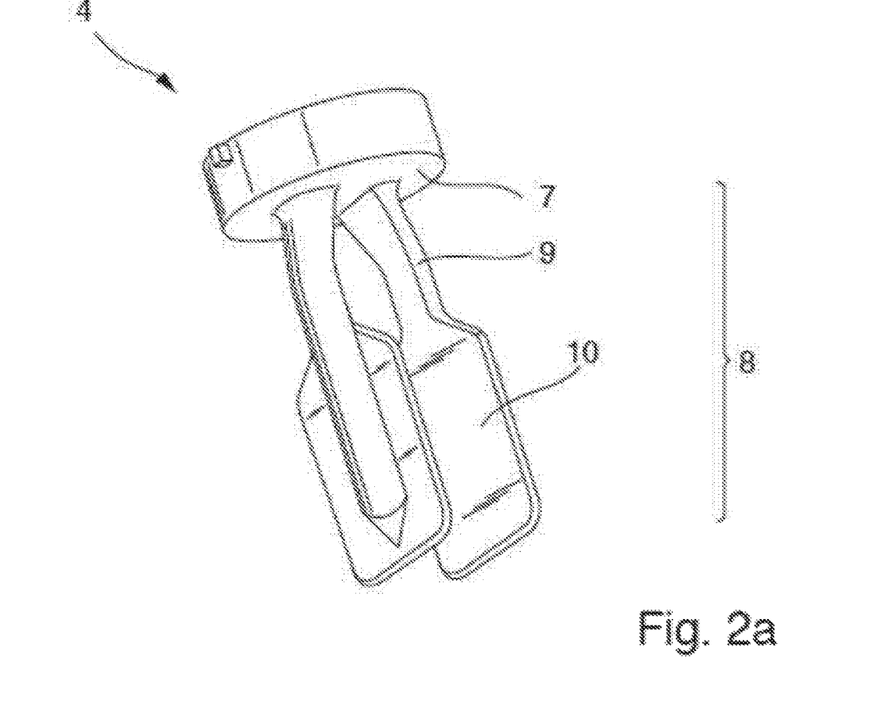
Figure 2B:
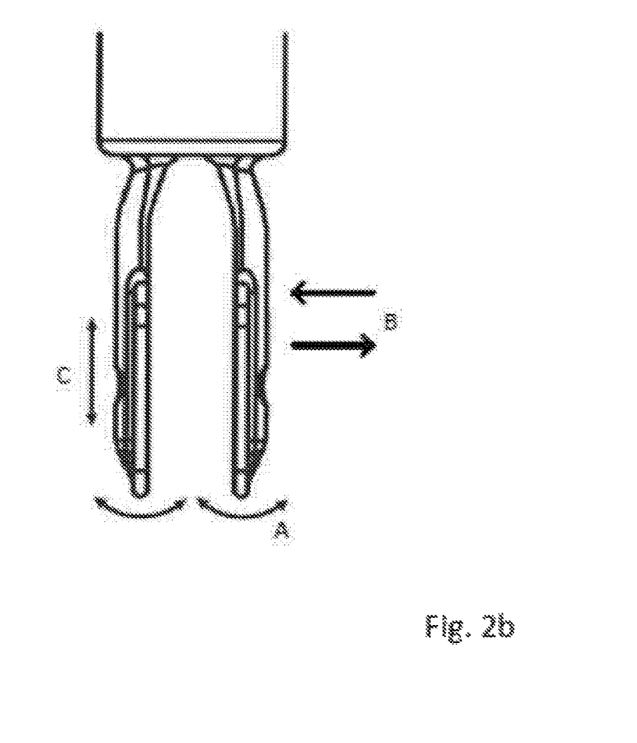

FIG. 2a shows schematically an oscillatory fork, such as used with the LIQUIPHANT field device. Shown is the membrane 7, and the oscillatory element 8 connected therewith. The oscillatory element includes two oscillatory rods 9, on the end of each of which a paddle 10 is formed. In operation, the oscillatory fork 4 executes oscillatory movements corresponding to the oscillatory mode, with which it is excited. How these movements look is shown schematically in FIG. 2b. Shown there is an oscillatory fork 4 turned by 90° relative to FIG. 2a. The arrows indicate the essential movement directions of the oscillatory fork 4 for the fundamental oscillation mode A, the first higher oscillatory mode B and the second higher oscillatory mode C. Each of the two oscillatory rods 9 behaves essentially as the bending oscillator mentioned in the introduction of the description. In the fundamental oscillation mode, the two oscillatory rods 9 oscillate with phase opposite to one another.

Figure 3A:
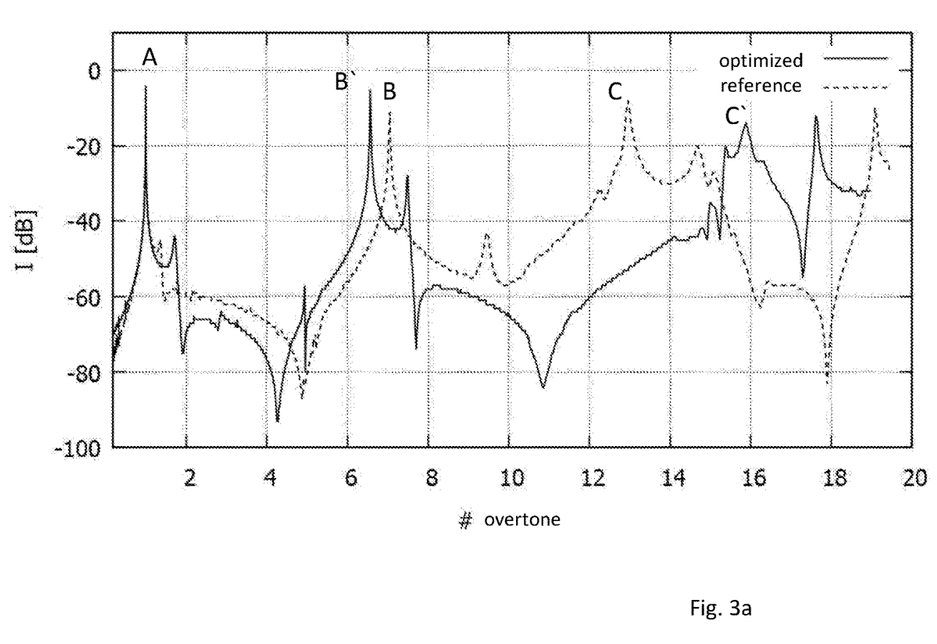
Figure 3B:
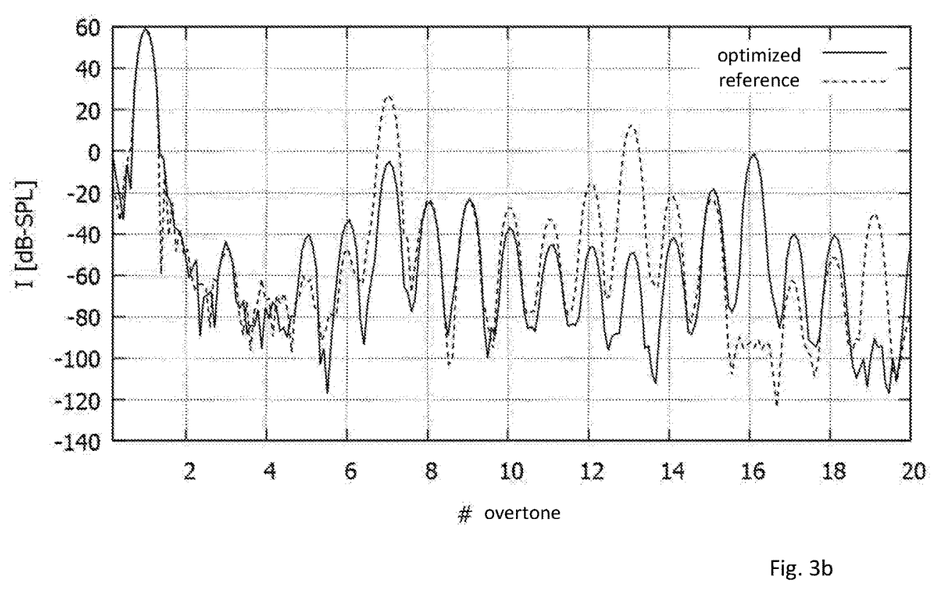

In FIG. 3a), finally, two oscillation spectra are shown, one for a conventional oscillatory fork in the LIQUIPHANT field device, and the second for an oscillatory fork of the invention. Both curves are normalized to whole-numbered multiples of the fundamental frequency, which corresponds to the fundamental oscillation mode. The dashed line is for the oscillation spectrum of the oscillatory fork in the LIQUIPHANT field device with the fundamental oscillation mode A at $1f_0$, the first higher oscillatory mode B in the vicinity of $7f_0$ and the second excited oscillatory mode in the vicinity of $13f_0$. In contrast, the first higher oscillatory mode B' for an oscillatory fork of the invention (solid line) lies at about $6.5f_0$, and, thus in the range between two whole-numbered multiples of the fundamental frequency and is no longer excited by the exciter signal. The second higher oscillatory mode C' of the oscillatory fork of the invention lies just about at $16f_0$, and, thus, in the region of the audible limit. The result is a clearly reduced noise emission of the oscillatory fork, such as is evident from the acoustic spectra in FIG. 3b) associated with the oscillation spectra. The decrease of the sound pressure for the first higher oscillatory mode B amounts to 32 dB(SPL) and that for the second higher oscillatory mode to 62 dB(SPL).

For manufacture of an optimized oscillatory fork of the invention, the mass distribution, the stiffness as well as the geometry were adapted by means of the finite elements method. In this regard, the mass distribution of the paddles was varied for shifting the first higher oscillatory mode B. For the second higher oscillatory mode C, in contrast, the radii in the transition region between the fork root and the membrane were varied, so that the stiffness as well as the bend line of the membrane, respectively the contact region between the oscillatory rod and the membrane, change.

Figure 4A:
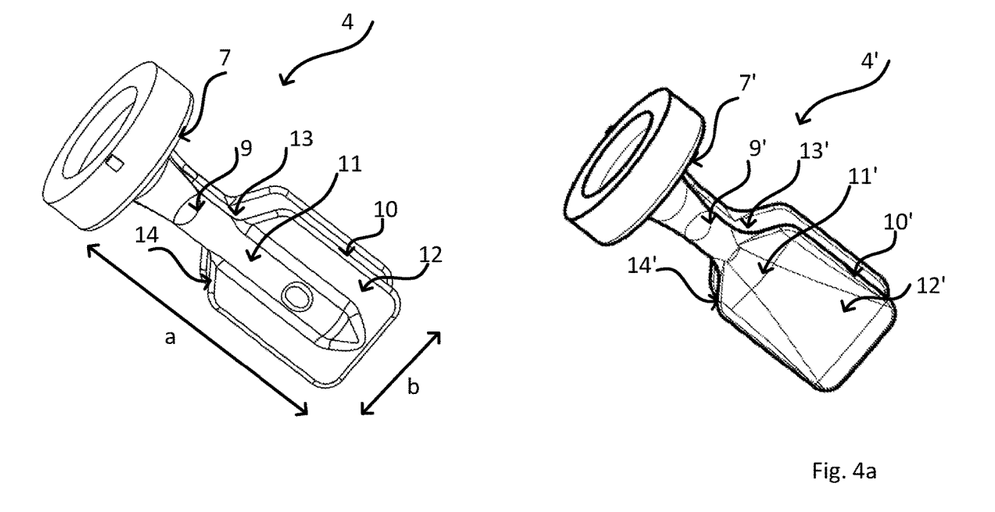
FIGS. 4a and 4b show a comparison of the geometries of the oscillatory fork of a LIQUIPHANT field device and an oscillatory fork of the invention belonging to the spectra in FIGS. 3a and 3b.
Figure 4B:
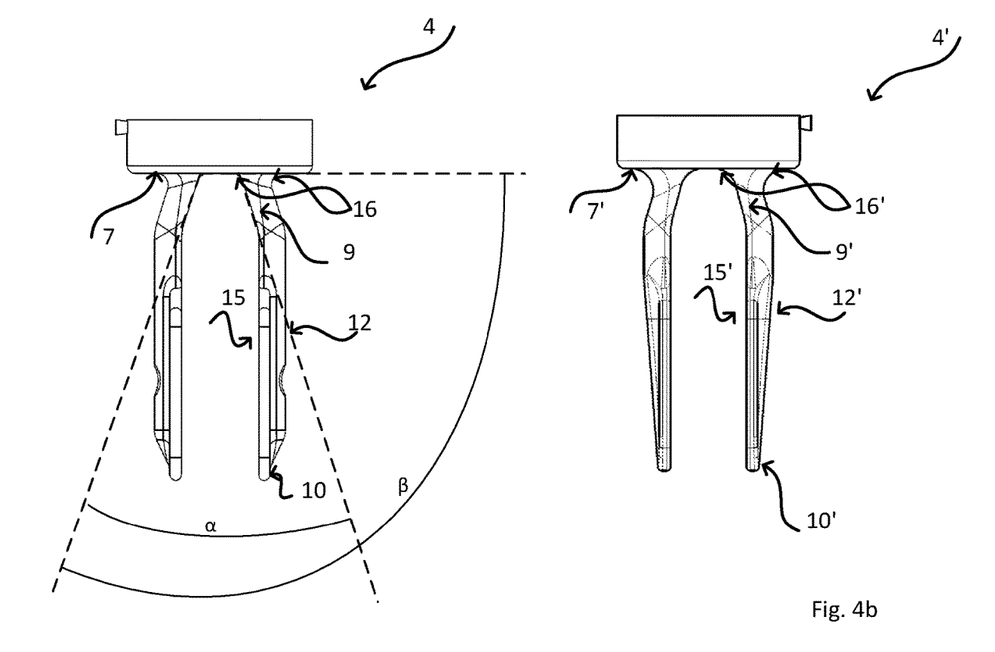

For illustration, a conventional LIQUIPHANT oscillatory fork 4 and an oscillatory fork of the invention 4' are placed alongside one another in FIG. 4. The figures, in each case, on the left represent the oscillatory fork in the LIQUIPHANT field device, while those on the right side are an embodiment of the invention. Furthermore, the reference characters, which refer to the embodiment of the invention, are provided with primes. The construction shown here is only one possible example of an oscillatory fork of the invention. There are countless other embodiments for oscillatory forks, which likewise would fall within the scope of the present invention.

On the left, in each case, are representations of the oscillatory fork in the LIQUIPHANT field device and on the right an analogous representation of an oscillatory fork of the invention. Depending on the process, some features of the conventional oscillatory fork in the LIQUIPHANT field device are maintained. These relate, on the one hand, to the length a of the membrane up to the end of the paddle at 40 mm, as well as width b of the paddle at 17.2 mm. Especially, attention was paid that the switching point of the oscillatory fork, correspondingly a frequency shift at a certain immersion depth into the medium, is not changed by the changes of the mass distribution and stiffness. It is understood, however, that here also other measures can be used for the oscillatable unit 8 and especially other switching points defined. FIG. 4a) provides a perspective view of the two oscillatory forks 4, 4'. For reasons of simplification, the following description is of only one of the two paddles 10,10'. The other paddle 10,10' is analogously embodied. While for the conventional oscillatory fork 4 (left), the oscillatory rod 9 continues along the paddle 10 as rib 11, which protrudes out from the paddle surface, in the case of the oscillatory fork 4' of the invention (right), the paddle 10' and the rib 11' merge to a homogeneous unit with curved surface, in which the oscillatory rod 9' transitions homogeneously. The outer paddle surface 12 of the oscillatory fork 4 in the LIQUIPHANT field device is planar with superimposed rib 11, while for the oscillatory fork 4' of the invention, the outer surface of the paddle 12' is curved and merged with the rib 11' and, thus, a homogeneous unit is formed. As a result of this merging, also the radius 13, respectively 13', changes at the transition between oscillatory rod 9, 9' and paddle 10,10', as well as the paddle upper edge contour 14, respectively 14', which is rounded for the oscillatable unit 4' of the invention.

FIG. 4b) shows the oscillatable units 4, 4' in a side view. In this representation, the differences between the outer surfaces 12, 12' of the paddles 10,10' can be yet better appreciated. For the oscillatory fork 4 in the LIQUIPHANT field device, the outer surface is planar, and for the oscillatory fork of the invention 4' curved. In the here shown embodiment, the inner surfaces 15,15' of the paddles are planar both for the oscillatory fork 4 and for the oscillatory fork 4'. It is understood, however, that also the inner surface of the paddle 15' can be curved.

A further difference between the two oscillatory forks 4, 4' relates to the angular orientations of the oscillatory rods 9,9' at the joints 16, 16' with the membranes 7,7'. This change can best be given by statement of the angles α and β, which are drawn for the oscillatory fork 4 of the LIQUIPHANT field device. These angles for the oscillatory fork 4 in the LIQUIPHANT field device are α=35.5°, and β=107.7° while for the oscillatory fork 4' of the invention, the analogous angles are α'=29.9° and β'=104.9°.

On the whole, for the shown example of an oscillatable unit 4' of the invention, the adapting of the mass distribution in the region of the paddle 10', which results from the merging of the rib 11' with the paddle surface, as well as the adapting of its curvature, effects the shifting of the first higher harmonic B. The shifting of the second higher harmonic C, in contrast, results from the adapting of the radii in the region of the joint 16, 16' with the membrane and the changed angular orientation.

Figure 5A:
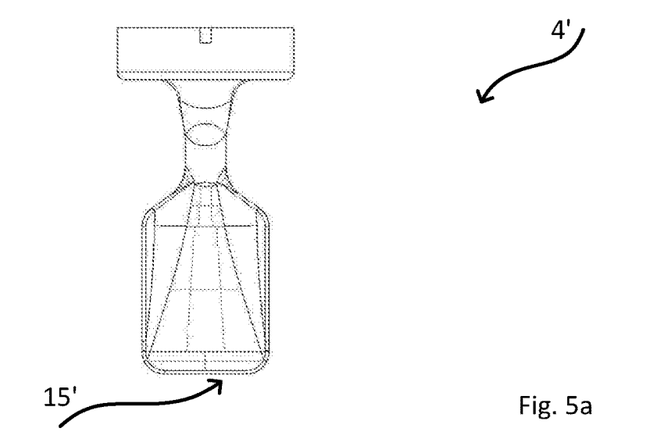
Figure 5B:
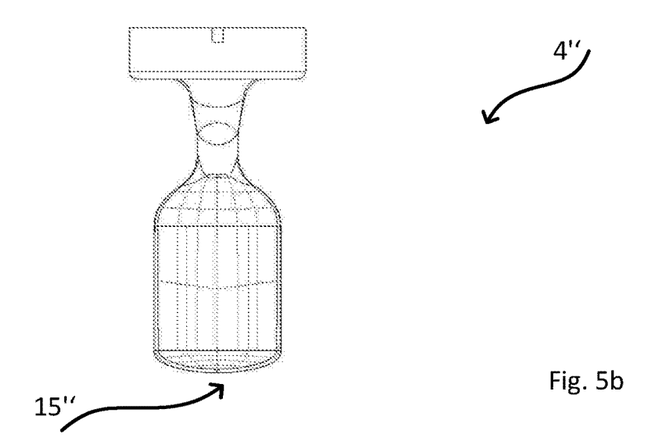
Figure 5C:
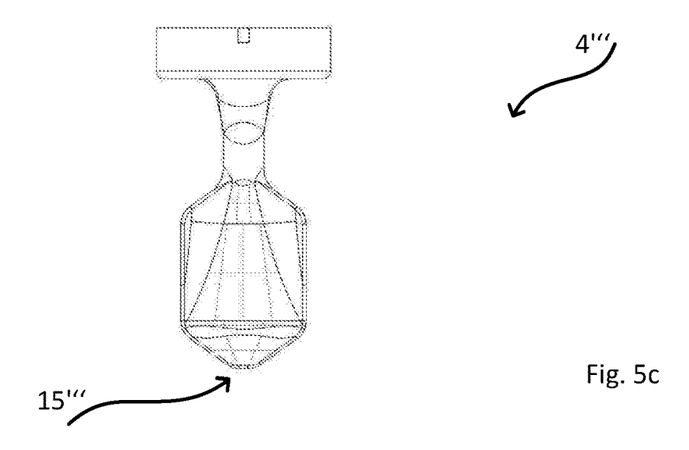

FIG. 5 shows, finally, two other variants of an oscillatory fork of the invention. Again, these are individual examples, and it is understood that besides these illustrated embodiments, there are still innumerable other variants, which can be designed and which all likewise fall within the scope of the invention. Here, FIG. 5a) shows a side view of an oscillatory fork 4' of the invention as shown in FIG. 4. The lower edge contour 15', i.e. the end region, of the paddle, is embodied straight in the case of this variant. In contrast, FIG. 5b) shows a possible embodiment of an oscillatory fork 4" of the invention with rounded lower edge contour 15", and FIG. 5c) an oscillatory fork 4' of the invention with a pointed lower end 15'''. Also, in the case of these examples, the process related measures a and b are maintained. These different geometries for the end regions 15', 15", 15''' of the paddles are motivated by the resulting differences in the drop shedding behavior. Rounded edge contours, 5" or such with a point 15''' have advantages in this regard. On the other hand, the change of the geometry of the end regions 15", 15' of the paddles changes also the sensitivity of the oscillatory forks, especially the switching point, so that, depending on choice of the end region 15',15",15''', the mass distribution and stiffness must be adapted anew.

The invention claimed is:

1. An apparatus for determining and/or monitoring at least one process variable of a medium in a container, comprising:
    a mechanically oscillatable unit having at least one membrane and at least one oscillatory element;
    a driving/receiving unit, which is embodied to excite said mechanically oscliiatable unit by means of an electrical, exciter signal of adjustable excitation frequency to execute oscillations in an oscillation mode corresponding to said excitation frequency and to receive mechanical oscillations from said mechanically osillatable unit and to convert such into an electrical received signal; and
    an electronics unit, which is embodied, based on said received signal, to produce said exciter signal, and to ascertain from said received signal said at least one process variable, wherein:
    said at least one membrane is connected with said driving/receiving unit;
    said at least one oscillatory element has the shape of an oscillatory rod, on which a paddle is terminally formed, said at least one oscillatory element is secured on said at least one membrane in an end region remote from said paddle; and
    a mass distribution, stiffness and/or geometry of said at least one oscillatable unit is/are selected in such a manner that at least one frequency corresponding to an oscillation mode of said at least one oscillatable unit higher in reference to a ground oscillation mode corresponding to a fundamental resonance frequency lies in the range between two neighboring whole-numbered multiples of said fundamental resonance frequency.

2. The apparatus as claimed in claim 1, wherein:
said oscillatable unit is an oscillatory fork.

3. The apparatus as claimed in claim 1, wherein:
said paddle is composed of a predeterminable material with a density ($\rho$), a predeterminable area ($A_P$) and a predeterminable thickness (d), and the product of thickness (d) and density ($\rho$) is as small as possible, and the area ($A_P$) of the paddle is as large as possible.

4. The apparatus as claimed in claim 3, wherein:
the area ($A_P$) of said paddle and/or of said oscillatory rod ($A_S$) is/are curved.

5. The apparatus as claimed in claim 3, wherein:
the width of said paddle (b) is greatest in the middle region with reference to the longitudinal axis (L) parallel to said oscillatory rod; and
said paddle in the end region remote from said membrane slopes at an angle between 20° and 55° to the longitudinal axis of said paddle.

6. The apparatus as claimed in claim 5, wherein:
said oscillatory rod has a round cross sectional area perpendicular to the longitudinal axis (L).

7. The apparatus as claimed in claim 3, wherein:
the thickness of said paddle in the end region is less than in the middle region.

8. The apparatus as claimed in claim 1, wherein:
edges of said paddle are rounded.

9. The apparatus as claimed in claim 8, wherein:
said paddle has a pointed end.

10. The apparatus as claimed in claim 1, wherein:
the at least one process variable is a predetermined fill level of the medium, or the density of the medium or the viscosity of the medium.

11. The apparatus as claimed in claim 1, wherein:
said oscillatable unit is composed of a metal, a ceramic or a synthetic material.

* * * * *